United States Patent
Takahashi et al.

(10) Patent No.: US 6,783,501 B2
(45) Date of Patent: Aug. 31, 2004

(54) HEART RATE MONITOR AND HEART RATE MEASURING METHOD

(75) Inventors: Yoshikazu Takahashi, Komoti-mura (JP); Wayne Baker, Shrewsbury, NJ (US); Hajime Shiogai, Komoti-mura (JP); Shinji Koshino, Komoti-mura (JP); Shintaro Mitsuhashi, Komoti-mura (JP)

(73) Assignee: Nihon Seimitsu Sokki Co., Ltd., Gunma-ken (JP)

( * ) Notice: Subject to any disclaimer, the term of this patent is extended or adjusted under 35 U.S.C. 154(b) by 0 days.

(21) Appl. No.: 10/185,718

(22) Filed: Jul. 1, 2002

(65) Prior Publication Data

US 2003/0018274 A1 Jan. 23, 2003

(30) Foreign Application Priority Data

Jul. 19, 2001 (JP) .................................. 2001-219993

(51) Int. Cl.[7] .............................................. A61B 5/02
(52) U.S. Cl. ...................................... 600/500; 600/479
(58) Field of Search ............................... 600/500, 476, 600/477, 479, 480, 481, 501, 502, 504, 507

(56) References Cited

U.S. PATENT DOCUMENTS

| | | | |
|---|---|---|---|
| 4,038,976 A | | 8/1977 | Hardy et al. |
| 4,223,680 A | * | 9/1980 | Jobsis ........................ 600/324 |
| 5,217,013 A | * | 6/1993 | Lewis et al. ................ 600/342 |
| 5,584,296 A | * | 12/1996 | Cui et al. ................... 600/479 |
| 5,673,692 A | * | 10/1997 | Schulze et al. ............. 600/301 |
| 5,902,235 A | * | 5/1999 | Lewis et al. ................ 600/323 |
| 5,954,053 A | * | 9/1999 | Chance et al. ............. 101/250 |
| 6,223,069 B1 | * | 4/2001 | Pfeiffer et al. ............. 600/431 |

FOREIGN PATENT DOCUMENTS

| | | |
|---|---|---|
| JP | 60-116325 A | 6/1985 |
| JP | 61-43057 B2 | 9/1986 |
| JP | 4-279146 A | 10/1992 |

* cited by examiner

*Primary Examiner*—Mary Beth Jones
*Assistant Examiner*—Navin Natnithithadha
(74) *Attorney, Agent, or Firm*—Venable LLP; Catherine M. Voorhees (57) ABSTRACT

Accurate occurrences of pulsation per unit time, that is, a heart rate is measured with a burden on a subject person being reduced to be very small and without being susceptible to body vibrations accompanying exercise. A heart rate monitor is produced, in which a light-emitting element 11 and a light-receiving element 12 are fitted to a head of a human body, light from the light-emitting element 11 is reflected at or transmitted through a subcutaneous artery 4 and/or blood running in the subcutaneous artery, the reflected or transmitted light is detected at the light-receiving element 12, and by using a CPU 14, the pulsation of the subcutaneous artery 4 and/or a change in bloodstream running in the subcutaneous artery 4 is measured from a change in intensity of the light detected at the light-receiving element 12, a pulse rate of the change in the bloodstream per unit time is calculated from this measured value, and the calculated pulse rate of the change in the bloodstream per unit time is regarded as a heart rate.

20 Claims, 5 Drawing Sheets

HEART RATE MONITOR AND HEART RATE MEASURING METHOD

BACKGROUND OF THE INVENTION

1. Field of the Invention

The present invention relates to a heart rate monitor for measuring the heart rate of a subject person while doing exercise such as running, jogging and walking, while doing light exercise, or during medical treatment.

It should be noted that the heart rate in this invention means "occurrences of pulse per unit time".

2. Description of the Related Art

As a method of measuring a heart rate, there are conventionally a method of detecting an electrocardiographic signal from electrodes attached to an area near a heart as disclosed in Japanese Patent Application Laid-open No. 60-116325, a method of optically detecting a pulse rate from a blood vessel of a lobe as disclosed in Japanese Patent Application Publication No. 61-43057, a method of detecting pressure pulsation by mechanical vibration from an artery near a body surface as disclosed in U.S. Pat. No. 4,038,976, and a method in combination with a hemodynamometer as disclosed in Japanese Patent Application Laid-open No. 4-279146.

However, the prior arts described above have the following problems to be solved.

Specifically, at first, in the method of detecting an electrocardiographic signal from electrodes attached to an area near a heart, it is necessary to fix the electrodes for detecting an electrocardiographic signal in contact with the skin of a thorax, and thus a band with a stretching properties, wound around the thorax is usually used. For this reason, a subject person has to be naked temporarily so that this band can be attached to him or her, and the chest is secured with such strength as to prevent this band from falling off, which sometimes gives a feeling of strain to the subject person if it is attached to him or her for a long period of time. Further, even if a heart rate is measured by the electrocardiographic signal collected at the thorax, in order to transmit it to the subject person, it is necessary to provide a display unit at a wrist or the like and send a signal to the wrist from the thorax by means such as radio.

Next, in the method of optically detecting a pulse rate from a blood vessel of a lobe, if a subject person does hard exercise such as running, there is the possibility of a measurement error occurring when the pulse rate is optically detected under the influence of body vibrations.

Even if the pulse rate is to be measured at a blood vessel where arteriovenous anastomosis exists as the blood vessel of a lobe, the aforementioned arteriovenous anastomosis has the function of adjusting bloodstream based on correlation between outside temperature and body heat, and therefore the bloodstream is decreased by this adjustment function to make the measurement difficult in some cases.

Further, in the method of detecting pressure pulsation by mechanical vibration from an artery near a body surface, body vibration has more influence than in the aforementioned method of optically detecting a pulse rate, and there is the possibility that a measurement error becomes large especially in the pulse rate detection during exercise.

In addition to it, in the method of performing detection in combination of a hemodynamometer, measurement can be made comparatively easily because a pulse rate is detected by an optical method or the like while a blood vessel is pressed with a cuff or the like. However, the burden that a measured region is pressed by the cuff or the like is imposed on the subject person during measurement.

In blood pressure measurement, the measurement is finished in a short time, and it is allowable that the measured region is pressed during that time. However, since heart rate measurement continues for a long time and measurement is needed during exercise, it is not preferable that the measured region is pressed by a cuff or the like.

The present invention is made in the aforementioned background, and is to provide a heart rate monitor, which imposes a very small burden on a subject person, is less susceptible to body vibrations accompanying exercise, and can measure the accurate occurrences of pulse per unit time, that is, a heart rate.

SUMMARY OF THE INVENTION

In order to solve the above-described disadvantage, trials and errors were repeated about taking out an accurate heart rate, with a burden on a subject person and a hindrance to exercise being made the smallest necessary limit, even under body vibrations of a subject person, and as a result, the present inventors have reached the following knowledge.

Specifically, in order to take out a heart rate with a burden on a subject person and a hindrance to exercise being made the smallest necessary limit even under the body vibrations of the subject person, it is preferable to reflect or transmit light at or through a blood vessel and/or blood, and thereafter detect the light.

Next, in order to collect an accurate heart rate, a thick artery in which arteriovenous anastomosis does not adjust bloodstream is preferable as a blood vessel at which the heart rate is taken out.

The present inventors have completed the invention of a heart rate monitor which can measure an accurate heart rate with a burden on a subject person and a hindrance to exercise being made the smallest necessary limit based on the above-described knowledge.

Specifically, a first aspect of the invention is a heart rate monitor comprising a light-emitting element, a light-receiving element, and a CPU, with light from the aforesaid light-emitting element being reflected at or transmitted through blood running in a blood vessel, the aforesaid light-receiving element detecting the reflected or transmitted light, the aforesaid CPU measuring a change in bloodstream running in the vessel from a change in intensity of the light detected at the aforesaid light-receiving element, and the aforesaid CPU calculating a pulse rate of the change in bloodstream per unit time from the measured value, and regarding the calculated pulse rate of the change in the bloodstream per unit time as a heart rate, and is characterized in that the aforesaid light-emitting element and the aforesaid light-receiving element are fitted to a head of a human body having a space of 4 mm to 10 mm between them, and light with a wavelength of 900 nm to 1200 nm emitted by the aforesaid light-emitting element is reflected at or transmitted through a subcutaneous artery and/or blood running in the subcutaneous artery and is detected at the aforesaid light-receiving element.

A second aspect of the invention is the heart rate monitor described above, which further comprises a display unit for displaying the calculated heart rate, and characterized in that the aforesaid display unit transmits the calculated heart rate to a measuring person and/or a subject person by means of a display, a voice, radio, and/or bone conduction.

A third aspect of the invention is the heart rate monitor which further comprises a storage device for storing the calculated heart rate.

A fourth aspect of the invention is the heart rate monitor which further comprises a head band fitted to a head of a human body, and characterized in that the aforesaid light-emitting element, the aforesaid light-receiving element, the aforesaid CPU, and the aforesaid display unit are attached to the aforesaid head band.

A fifth aspect of the invention is the heart rate monitor which further comprises an eyeglass frame fitted to a head of a human body, and characterized in that the aforesaid light-emitting element, the aforesaid light-receiving element, the aforesaid CPU and the aforesaid display unit are attached to the aforesaid eyeglass frame.

A sixth aspect of the invention is the heart rate monitor which further comprises a sun visor fitted to a head of a human body, and characterized in that the aforesaid light-emitting element, the aforesaid light receiving element, the aforesaid CPU and the aforesaid display unit are attached to the aforesaid sun visor.

A seventh aspect of the invention is the heart rate monitor which further comprises a container engaged in an ear pinna of a human body, and characterized in that the aforesaid light-emitting element, the aforesaid light-receiving element, the aforesaid CPU and the aforesaid display unit are attached to the aforesaid container.

An eighth aspect of the invention is a method of measuring a heart rate comprising the steps of fitting a light-emitting element and a light-receiving element to a human body, reflecting or transmitting light emitted by the aforesaid light-emitting element at or through blood running in a blood vessel and detecting it at the aforesaid light-receiving element, measuring a change in bloodstream running in the blood vessel from a change in intensity of the light detected at the aforesaid light-receiving element, and calculating a pulse rate of the change in bloodstream per unit time from the calculated value and regarding the calculated pulse rate of the change in blood stream per unit time as a heart rate, and is characterized in that the aforesaid light-emitting element and the aforesaid light-receiving element are fitted to a head of a human body with a space of 4 mm to 10 mm between them, and light with a wavelength of 900 nm to 1200 nm emitted by the aforesaid light-emitting element is reflected at or transmitted through a subcutaneous artery and/or blood running in the subcutaneous artery and is detected at the aforesaid light receiving element.

DETAILED DESCRIPTION OF THE PREFERRED EMBODIMENT

A preferred embodiment of the present invention will be explained in detail below.

First, as described above, in order to take a heart rate with a burden on a subject person and hindrance to exercise being reduced to the minimum necessary amount, it is preferable to reflect or transmit light at or through a blood vessel and/or blood and thereafter detect the light. In order to take an accurate heart rate, a thick artery for which arteriovenous anastomosis does not adjust bloodstream is preferable as a blood vessel from which the heart rate is taken.

However, since a thick artery of a human body is not normally located near a body surface, the accurate heart rate cannot be taken even if light is emitted from the body surface to try to detect the light after reflected or transmitted at or through the artery in a non-pressed state.

Here, a first conception of the present inventors is that they paid attention to a subcutaneous artery at a head of a human body as a blood vessel where the heart rate is taken. Normally, thick arteries are located in a deep inside of a human body as described above, but in the head, they are located comparatively near the body surface.

Specifically, thick arteries exist in soft tissue between cranial bones and a skin, and less fat tissue causing a hindrance to measurement exists in the soft tissue irrespective of physique of subject persons.

More preferably, the most stable spot in a human body during exercise such as running is a head of a human body. This is considered to protect the brain from shock during exercise, and as a place where data is stably taken from a human body during the exercise, the head is also the most suitable place.

To be additionally preferable, functional parts for transmitting a heart rate obtained by processing the obtained data to a subject person are reduced in size and weight as a result of improvement in electronics. Since the obtained heart rate is transmitted to eyes or ears of the subject person by means of light or voice, if the data is taken at the head, a heart rate monitor with everything being integrated and excellent in operability can be realized.

Next, a second conception of the present inventors is that they found out an optimal wavelength of light of a light-emitting element and an optimal distance between the light-emitting element and a light-receiving element.

Specifically, light with a wavelength of 900 nm to 1200 nm, more preferably, 950 nm to 1050 nm, penetrates in a human body favorably and is modulated by the movement of an artery and bloodstream. Further, the distance between the light-emitting element and the light receiving element is made to be 4 mm to 10 mm, more preferably, 7 mm to 9 mm, whereby the aforementioned modulated light can be favorably detected.

Preferred embodiments of the present invention will be explained in more detail below with reference to the drawings.

Figure 1:
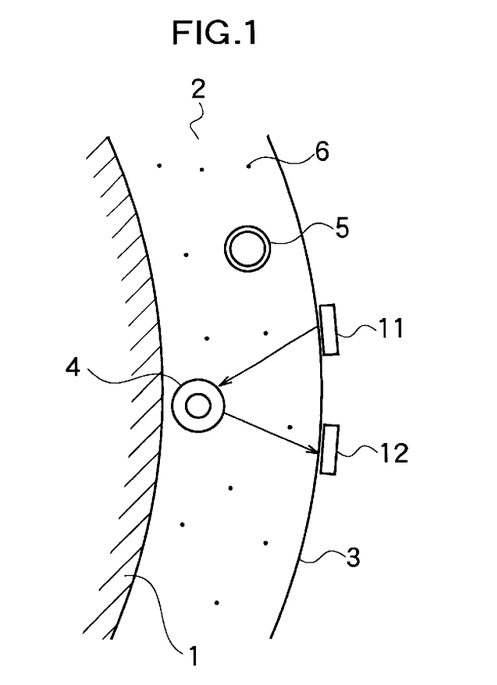
FIG. 1 is a schematic diagram of a section in a surface of a head of a subject person.

FIG. 1 is a schematic diagram of a section in a surface of a head of a subject person.

Soft tissue 2 exists between cranial bones 1 and a skin 3, and for example, an artery 4 such as a supraorbital artery and a vein 5, and a capillary vessel 6 exist in the soft tissue, and a light-emitting element 11 and a light-receiving element 12 are provided on the skin 3.

Blood runs in the artery 4, the vein 5 and the capillary vessel 6, and the artery 4 especially pulsates in accordance with a heart rate.

The light-emitting element 11 is preferably an infrared LED or the like generating light having a wavelength of 900 nm to 1200 nm, more preferably, 950 nm to 1050 nm. This is because the infrared light with the wavelength is hardly absorbed in body tissue and transmits through the soft tissue 2 to reach the artery 4 and the like, whereby it is modulated and reflected, and can be detected at the light receiving element 12. It should be noted that as the light-receiving element 12, a photo transistor or the like can be appropriately used.

Further, it is preferable that the light-emitting element 11 and the light-receiving element 12 are placed on the skin 3 with a space of 4 mm to 10 mm, more preferably, 7 mm to 9 mm between them.

This is because it is preferable that the space between both the elements is small in order to detect the light emitted from the light-emitting element 11 and reflected at the artery 4 by the light-receiving element 12, but it is difficult to place both the elements directly above the artery 4 or in the state in which both the elements straddle the artery 4 for each measurement, and further the location of the artery 4 differs a little among individuals and the like. Therefore, when the light-emitting element 11 and the light-receiving element 12 have the space of 4 mm to 10 mm, more preferably, 7 mm to 9 mm, the light reflected from the artery 4 can be received with stability. Further, it is also preferable to increase the number of the light-receiving elements to be two or more and provide them around the light-emitting element 11 as a center to thereby efficiently and stably receive the reflected light from the artery 4 and perform comparative processing of signals from a plurality of the light-receiving elements, thereby making the constitution in which an influence of outer light is cancelled.

In addition to the above, an artery near an external auditory meatus can be used as placement positions for the light-emitting element 11 and the light-receiving element 12.

This makes the constitution in which light is emitted to a superficial temporal artery existing in this region and the reflected or transmitted light is detected, and it is possible to adopt the constitution in which the light-emitting element 11 and the light-receiving element 12 are placed at the superficial temporal artery side in an external ear with a space being provided between them as described above, or to adopt the constitution in which the light-emitting element 11 is placed inside the external auditory meatus and the light-receiving element 12 is placed at a side across the superficial temporal artery.

Figure 2:
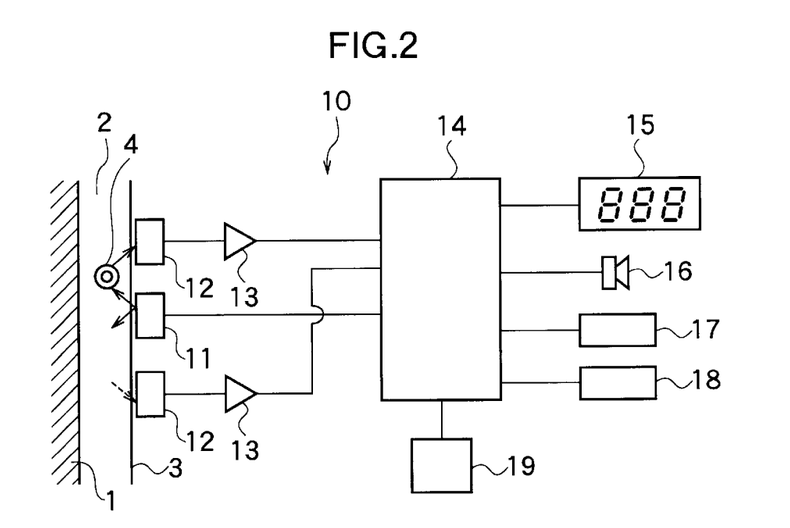
FIG. 2 is a circuit block diagram of a heart rate monitor according to an embodiment.

FIG. 2 is a circuit block diagram in a heart rate monitor 10 according to the present invention.

Light generated from the light-emitting element 11 is pulsation-modulated and reflected at an artery of a human body, and is detected by the light-receiving element 12 to be an electric signal. The obtained electric signal is appropriately amplified in an amplifier 13 to enter a CPU 14. At this time, it is a preferable constitution that the light-emitting element 11 is not lit all the time but lit in a pulse form to save electric power, thereby increasing the life of a battery in the heart rate monitor 10.

The CPU 14 compares a signal sent to the light-emitting element 11 and the modulated electric signal detected at the light-receiving element 12, then cancels a disturbance factor such as outer light, and measures pulsation of a subcutaneous artery and/or a change in bloodstream in the subcutaneous artery. Subsequently, the CPU 14 calculates the pulse rate in the change of bloodstream per unit time from the measured pulse rate and the like, and this is regarded as a heat rate.

Further, the CPU 14 converts the calculated heart rate into a numerical value, and transmits it to the subject person and/or a measuring person via a display unit.

As a concrete transmitting method, it is preferable to transmit the calculated heart rate to the subject person and the like by optically displaying it on a display 15, by converting the heart rate in the numerical form into a synthetic voice and running it into an earphone 16, by running the heart rate in the synthetic voice to a bone conduction element 17 and/or the like.

Further, as necessary, the constitution in which the data of the heart rate is transmitted from a transmitter 18 by radio or the like and received by a receiver at the measuring person may be suitable.

In addition, it is a preferable constitution that the CPU 14 is provided with a data storage device 19.

By adopting this constitution, a heart rate measurement value within a desired period of time can be temporarily stored in the data storage device 19. By reading and analyzing the temporarily stored data by a computer or the like, it is made possible to obtain data contributing to the grasp of capacity of locomotion, physical condition and the like of a subject person without being limited by a measuring time.

FIG. 3 through FIG. 7 show examples of devices of the heart rate monitor 10 having the aforementioned constitution and examples of fitting them to a subject person.

(Fitting Example 1)

Figure 3:
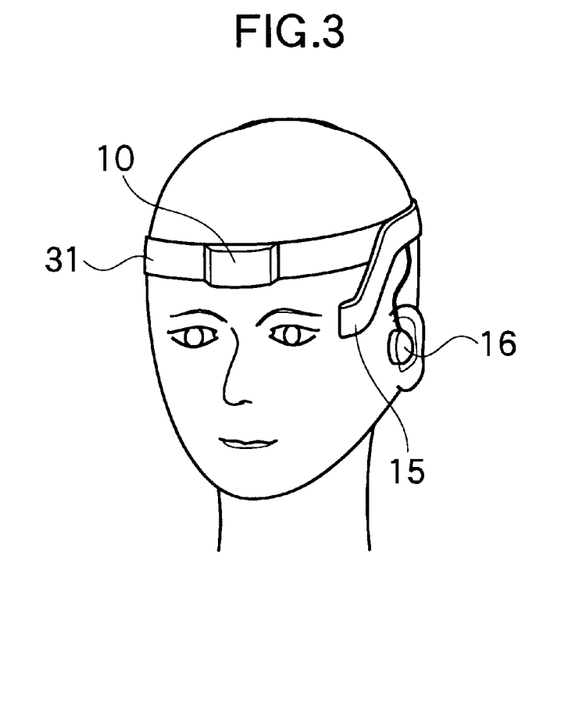
FIG. 3 is a perspective view of a fitting example of the heart rate monitor according to the embodiment to a subject person.

FIG. 3 shows an example in which the heart rate monitor 10, the display 15 and the earphone 16 are placed at a head band 31 wound around a head of a human body.

In this example, if the heart rate monitor 10 is placed at a brow, a supraorbital artery or the like can be used as an artery at which the heart rate is detected, and if it is placed at a temporal region, a superficial temporal artery, zygomatico-orbital artery or the like can be used.

The display 15 using liquid crystal or the like as a display unit may be used, but it is also a preferable constitution that with use of a head mount display, the displayed numerical value is transmitted to a subject person in a virtual reality form as if it were, for example, 50 cm ahead of him or her while the display itself actually exists near his or her eyes.

In this example, the display 15 and the earphone 16 are both provided, but the constitution in which either one is used may be suitable.

(Fitting Example 2)

Figure 4:
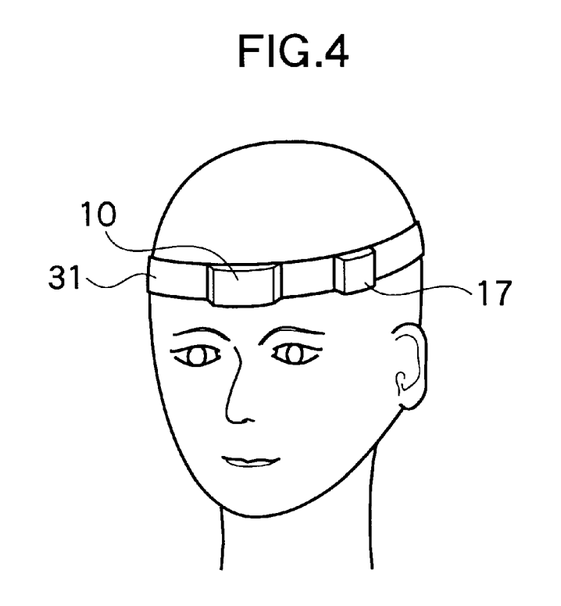
FIG. 4 is a perspective view of a fitting example of the heart rate monitor according to the embodiment to the subject person.

FIG. 4 shows an example in which the heart rate monitor 10 and the bone conduction element 17 are placed at the head band 31 as shown in FIG. 3.

The bone conduction element 17 transmits a synthetic voice signal from the CPU 14 as a vibration, and therefore a subject person can hear the synthetic voice even if there is noise around him or her.

If this constitution is adopted, the heart rate monitor 10 and the bone conduction element 17 can be both placed on the head band 31, which can provide a simple design and is preferable in handling.

(Fitting Example 3)

Figure 5:
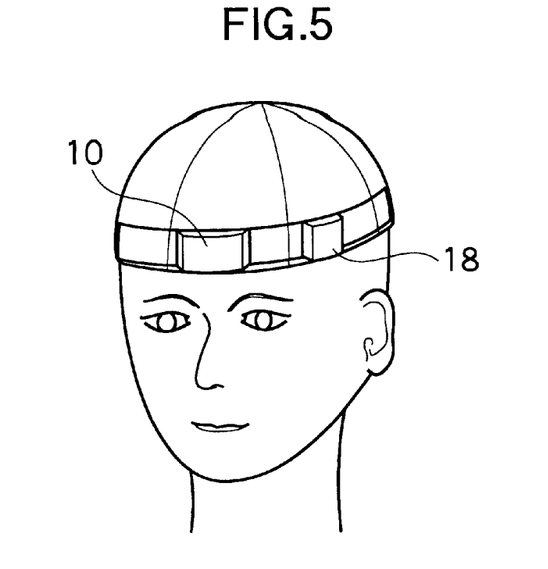
FIG. 5 is a perspective view of a fitting example of the heart rate monitor according to the embodiment to the subject person.

FIG. 5 shows an example in which the heart rate monitor 10 and the transmitter 18 are placed on the head band 31 as shown in FIG. 3.

The transmitter 18 transmits a heart rate signal from the CPU to the receiver by radio.

The constitution in which the heart rate signal received at the receiver can be, for example, further stored, printed, displayed and analyzed can be provided. In order to feed back the date to the subject person, the constitution using an optical display or a synthetic voice is preferable.

If this constitution is adopted, the heart rate monitor 10 and the transmitter 18 can be both placed on the head band 31, which can provide a simple design, and is preferable in handling.

Here, the aforementioned (Fitting example 2) and (Fitting example 3) are the fitting examples suitable for heart rate measurement on the occasion of doing sports such as, for example, swimming, athletic sports, and a ball game, which give a shock to a head or require vigorous motions.

It is a preferable constitution that the head band 31 provided with the heart rate monitor 10 and the like is integrated with, for example, a swimming cap to further reduce a burden on a subject person, for the heart rate measurement on the occasion of swimming.

(Fitting Example 4)

Figure 6:
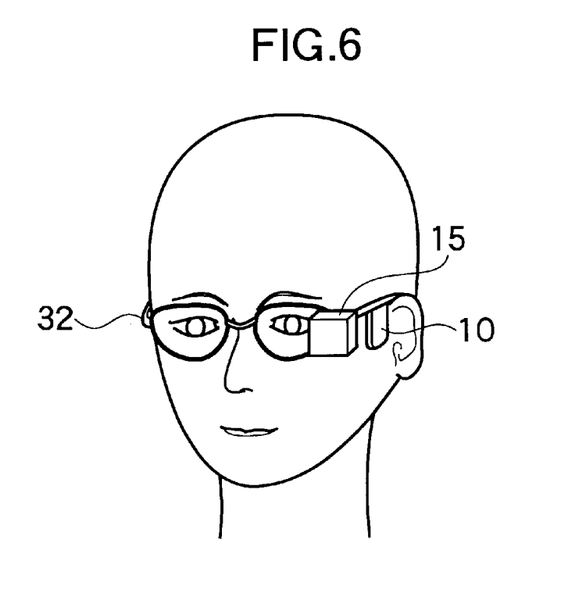
FIG. 6 is a perspective view of a fitting example of the heart rate monitor according to the embodiment to the subject person.

FIG. 6 is an example in which the heart rate monitor 10 and the display unit are placed at an eyeglass frame 32.

In this example, the heart rate monitor 10 is placed at a temple part of the eyeglass frame 32, and therefore a superficial temporal artery, a zygomatico-orbital artery and the like can be used as an artery at which the heart rate is detected. As the display unit, the display 15 using liquid crystal or the like as in the example shown in FIG. 3 may be used, but the constitution in which a head mound display is used is also preferable.

It goes without saying that the earphone 16 and/or the bone conduction element 17 can be used.

(Fitting Example 5)

Figure 7:
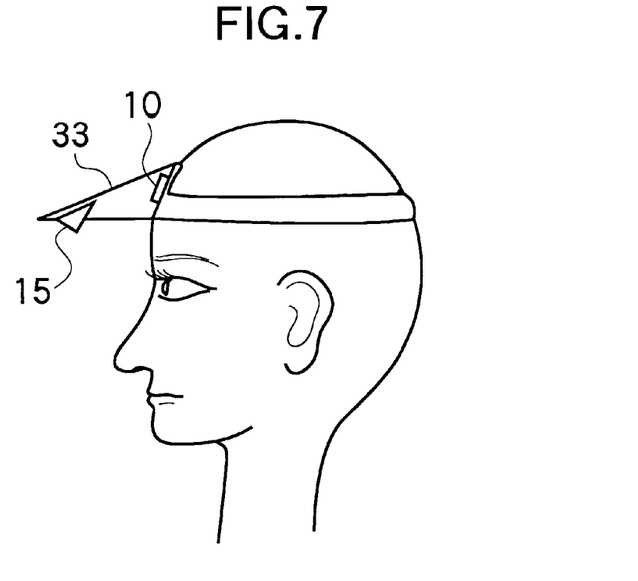
FIG. 7 is a perspective view of a fitting example of the heart rate monitor according to the embodiment to the subject person.

FIG. 7 is an example in which the heart rate monitor 10 and the display unit are placed at a sun visor 33.

In this example, the heart rate monitor 10 is placed at a brow region or temporal region with use of the sun visor 33, and therefore a supraorbital artery, a superficial temporal artery, a zygomatico-orbital artery and the like can be used as an artery at which the heart rate is detected. As the display unit, the display 15 using liquid crystal or the like as in the example shown in FIG. 3 may be used, but the constitution in which a head mound display is used is also preferable.

It goes without saying that the earphone 16 and/or the bone conduction element 17 can be used.

(Fitting Example 6)

Figure 8:
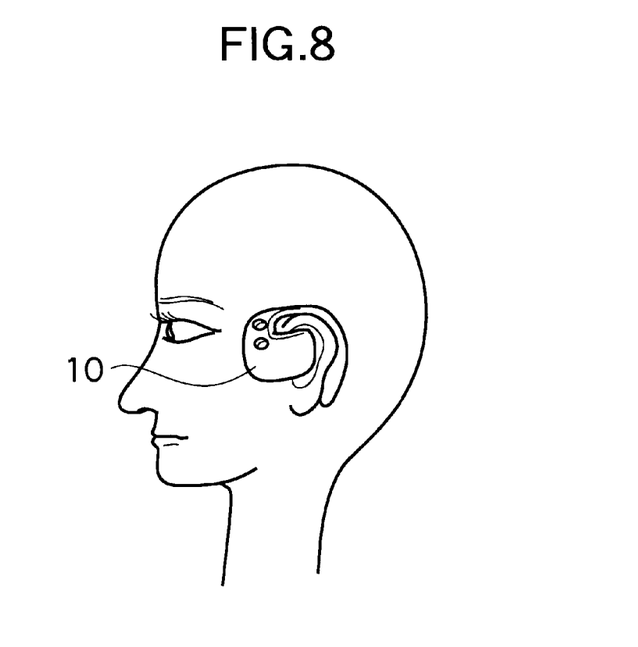
FIG. 8 is a perspective view of a fitting example of the heart rate monitor according to the embodiment to the subject person.

FIG. 8 is an example in which the heart rate monitor 10 itself is shaped into an ear attachment set and is engaged in an ear pinna.

Figure 9:
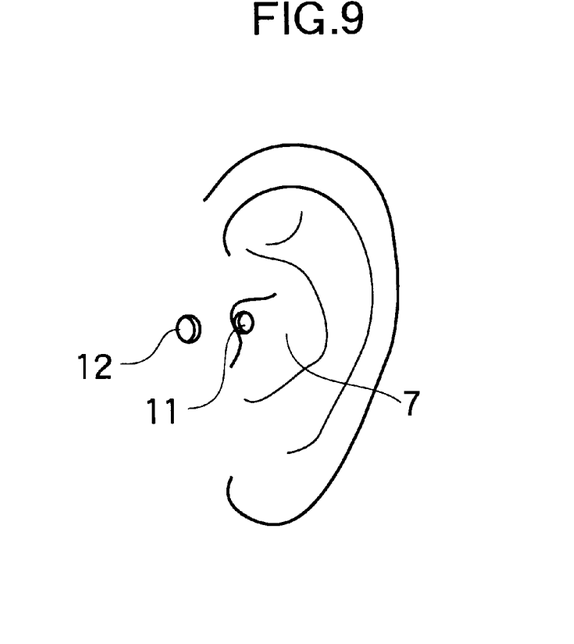
FIG. 9 is an example of the heart rate monitor according to the embodiment fitted to an ear of the subject person.
Figure 10:
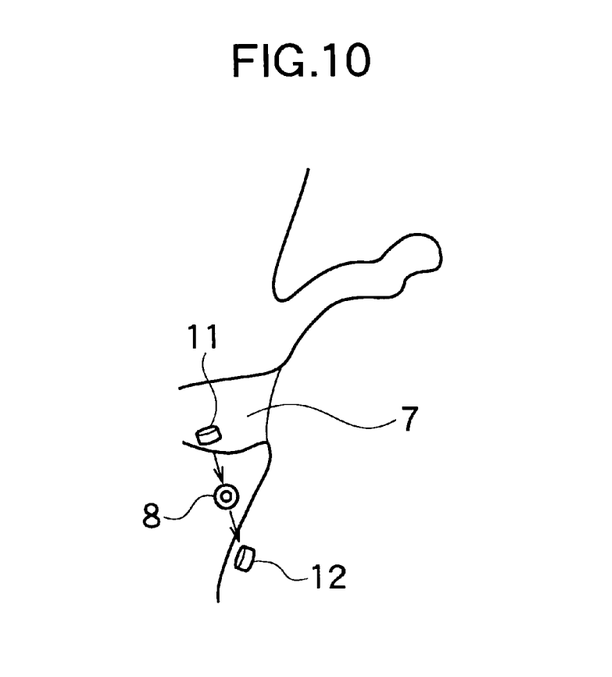
FIG. 10 is a schematic view of a cross section of an ear region of the subject person in the fitting example shown in FIG. 9.

In this example, the light-emitting element 11 is placed in an external auditory meatus 7 as shown in FIG. 9 and FIG. 10.

Here, FIG. 9 is a perspective view showing the situation in which the light-emitting element 11 and the light-receiving element 12 of the heart rate monitor 10 are placed with a posterior auricular artery 8 between them, and FIG. 10 is a schematic diagram of a cross section of the aforementioned light-emitting element 11 and the light-receiving element 12 being placed with the posterior auricular artery 8 between them.

As is obvious from FIG. 10, light emitted from the light-emitting element 11 is transmitted through the posterior auricular artery 8 to reach the light-receiving element 12. The heart rate can be obtained form the light reaching the light-receiving element 12.

When the light-emitting element 11 and the light-receiving element 12 are placed with the posterior auricular artery 8 between them, if the light-emitting element 11 is placed at a side of an external auditory meatus 7, a preferable constitution that is not susceptible to outer light is obtained.

Here, it is also a preferable constitution that the form of the ear attachment set is suitably designed to attach and integrate the light-emitting element 11, the light-receiving element 12, the CPU 14 and the earphone 16 inside a container of an ear attachment set to thereby reduce a burden on a subject person.

It is also a preferable constitution that a synthetic voice signal from the CPU 14 is transmitted to the subject person with use of the bone conduction element 17 integrated with the ear attachment set.

In the above-described fitting examples 1 through 6, it is also a preferable constitution that the data storage device 19 is provided in the CPU 14 as described above.

As described in detail thus far, the present invention has the object of measuring accurate occurrences of pulsation per unit time, that is, the heart rate, with a burden on a subject person being reduced to be very small, and without being susceptible to body vibrations accompanying exercise, and is to provide a heart rate monitor comprising a light-emitting element, a light-receiving element, and a CPU, with light from the aforesaid light-emitting element being reflected at or transmitted through blood running in a blood vessel, the aforesaid light-receiving element detecting the reflected or transmitted light, the aforesaid CPU measuring a change in bloodstream running in the blood vessel from a change in intensity of the light detected at said light-receiving element, and the aforesaid CPU calculating a pulse rate of the change in the bloodstream per unit time from the measured value, and regarding the calculated pulse rate of the change in the bloodstream per unit time as a heart rate, and is characterized in that the aforesaid light-emitting element and the aforesaid light-receiving element are fitted to a human head having a space of 4 mm to 10 mm between them, and light with a wavelength of 900 nm to 1200 nm emitted by the aforesaid light-emitting element is reflected at or transmitted through a subcutaneous artery and/or blood running in the subcutaneous artery and is detected at the aforesaid light-receiving element.

As a result, it becomes possible to measure an accurate heart rate with a burden on a subject person and a hindrance to exercise being the minimum necessary amount.

What is claimed is:

1. A heart rate monitor comprising a light-emitting element, a light-receiving element, and a CPU, light from said light-emitting element being reflected at or transmitted through blood running in a subcutaneous artery, said light-receiving element detecting the reflected or transmitted light, said CPU measuring a change in the bloodstream running in the a subcutaneous artery from a change in intensity of the light detected at said light-receiving element, and said CPU calculating a pulse rate of the change in the bloodstream per unit time from the measured value, and regarding the calculated pulse rate of the change in the bloodstream per unit time as a heat rate, wherein said light-emitting element and said light-receiving element are fitted to a human head and have a space of 4 mm to 10 mm between them, and wherein light with a wavelength of 900 nm to 1200 nm emitted by said light-emitting element is reflected at or transmitted through the subcutaneous artery and/or blood running in the subcutaneous artery and is detected at said light-receiving element.

2. The heart rate monitor according to claim 1, further comprising:

a display unit for displaying the calculated heart rate, wherein said display unit transmits the calculated heart rate to a measuring person and/or a subject person by means of an optical display, a voice, radio, and/or bone conduction.

3. The heart rate monitor according to claim 1, further comprising:

a storage device for storing the calculated heart rate.

4. The heart rate monitor according to claim 1, further comprising:

a head band fitted to the head of the human body, wherein said light-emitting element, said light-receiving element, said CPU, and said display unit are attached to said head band.

5. The heart rate monitor according to claim 1, further comprising:

an eyeglass frame fitted to the head of the human body, wherein said light-emitting element, said light-receiving element, said CPU and said display unit are attached to said eyeglass frame.

6. The heart rate monitor according to claim 1, further comprising:

a sun visor fitted to the head of the human body;

wherein said light-emitting element, said light-receiving element, said CPU and said display unit are attached to said sun visor.

7. The heart rate monitor according to claim 1, further comprising:

a container engaged in an ear pinna of the human body, wherein said light-emitting element, said light-receiving element, said CPU and said display unit are attached to said container.

8. The heart rate monitor according to claim 1, wherein the light-emitting element is arranged inside an ear canal of the human body, the light-receiving element being arranged outside the ear so that the subcutaneous artery is positioned between the light-emitting element and the light-receiving element.

9. The heart rate monitor according to claim 1, wherein the light-emitting element and light-receiving element are arranged to have an optical path from an internal portion of an ear of the human body to a position outside the ear where the subcutaneous artery is positioned in the optical path.

10. The heart rate monitor according to claim 1, wherein an arrangement of the light-emitting element and the light-receiving element has an optical path from an internal part of an ear to a position outside the ear where the subcutaneous artery is positioned between the light-emitting element and the light-receiving element.

11. A method of measuring a heart rate comprising the steps of:

fitting a light-emitting element and a light-receiving element to a head of a human body;

reflecting or transmitting light emitted by said light-emitting element at or through blood running in a subcutaneous artery and detecting it at said light-receiving element;

measuring a change in the bloodstream running inside the subcutaneous artery from a change in intensity of the light detected at said light-receiving element; and calculating a pulse rate of the change in the bloodstream per unit time from the measured value and regarding the calculated pulse rate of the change in the bloodstream per unit time as a heart rate, wherein said light-emitting element and said light-receiving element are fitted to the head of a human body and have a space of 4 mm to 10 mm between them, and wherein light with a wavelength of 900 nm to 1200 nm emitted by said light-emitting element is reflected at or transmitted through the subcutaneous artery and/or blood running in the subcutaneous artery and is detected at said light receiving element.

12. The heart rate monitor according to claim 2, further comprising:

a storage device for storing the calculated heart rate.

13. The heart rate monitor according to claim 2, further comprising:

a head band fitted to the head of the human body, wherein said light-emitting element, said light-receiving element, said CPU, and said display unit are attached to said head band.

14. The heart rate monitor according to claim 3, further comprising:

a head band fitted to a the head of a the human body, wherein said light-emitting element, said light-receiving element, said CPU, and said display unit are attached to said head band.

15. The heart rate monitor according to claim 2, further comprising:

an eyeglass frame fitted to the head of the human body, wherein said light-emitting element, said light-receiving element, said CPU and said display unit are attached to said eyeglass frame.

16. The heart rate monitor according to claim 3, further comprising:

an eyeglass frame fitted to the head of the human body, wherein said light-emitting element, said light-receiving element, said CPU and said display unit are attached to said eyeglass frame.

17. The heart rate monitor according to claim 2, further comprising:

a sun visor fitted to the head of the human body;

wherein said light-emitting element, said light-receiving element, said CPU and said display unit are attached to said sun visor.

18. The heart rate monitor according to claim 3, further comprising:

a sun visor fitted to the head of the human body;

wherein said light-emitting element, said light-receiving element, said CPU and said display unit are attached to said sun visor.

19. The heart rate monitor according to claim 2, further comprising:

a container engaged in an ear pinna of the human body, wherein said light-emitting element, said light-receiving element, said CPU and said display unit are attached to said container.

20. The heart rate monitor according to claim 3, further comprising:

a container engaged in an ear pinna of the human body, wherein said light-emitting element, said light-receiving element, said CPU and said display unit are attached to said container.

\* \* \* \* \*